United States Patent [19]

Persson et al.

[11] Patent Number: 4,556,010
[45] Date of Patent: Dec. 3, 1985

[54] METHOD OF CONTROLLING NOXIOUS INSECTS

[76] Inventors: Bert Persson; Håkan Svensson, both of Älggatan 47D, S-216 15 Malmö, Sweden

[21] Appl. No.: 438,873
[22] PCT Filed: Mar. 19, 1982
[86] PCT No.: PCT/SE82/00078
§ 371 Date: Sep. 30, 1982
§ 102(e) Date: Sep. 30, 1982
[87] PCT Pub. No.: WO82/03155
PCT Pub. Date: Sep. 30, 1982

[30] Foreign Application Priority Data

Mar. 20, 1981 [SE] Sweden ............................ 8101771

[51] Int. Cl.⁴ .............................................. G08B 1/00
[52] U.S. Cl. ...................................... 116/22 R; 43/113
[58] Field of Search ............................ 116/22 A, 22 R; 362/805, 811; 119/156; 43/132.1, 113

[56] References Cited

U.S. PATENT DOCUMENTS

| | | | |
|---|---|---|---|
| 697,072 | 4/1902 | Davis | 116/22 A |
| 1,483,710 | 2/1924 | Black | 362/811 |
| 1,819,551 | 8/1931 | Gourdon | 43/113 |
| 4,337,592 | 7/1982 | Hasegawa | 43/132.1 |
| 4,356,656 | 11/1982 | Tasma | 43/132.1 |

FOREIGN PATENT DOCUMENTS

| | | |
|---|---|---|
| 73091 | 9/1951 | Denmark. |
| 2375824 | 7/1978 | France. |
| 522357 | 6/1972 | Switzerland. |

OTHER PUBLICATIONS

Persson, B.—1971, Influence of Light on Flight Activity of Noctuids, (Lepidoptera) in South Sweden Ent. Scand. 2, pp. 215–232.

Persson, B.—1974, Diel Distribution of Oviposition in *Agrotis ipsilon* (Hufn.), *Agrotis munda* (Walk) and *Heliothis armigera* (Hbn.) in Relation to Temperature and Moonlight, Ent. Scand. 5, pp. 196–208.

Persson, B.—1976, Influence of Weather and Nocturnal Illumination on the Activity and Abundance of Populations of Noctuids (Lepidoptera) in South Coastal Queensland, Bull. Ent. Res. 66, pp. 33–63.

Persson, B.—1977, Distribution of Catch in Relation to Emergence of Adults in Some Noctuid Species in South Coastal Queensland, Austr. J. Zool. 25, pp. 95–102.

Primary Examiner—Steven L. Stephan
Assistant Examiner—Denis E. Corr
Attorney, Agent, or Firm—Merchant, Gould, Smith, Edell, Welter & Schmidt

[57] ABSTRACT

A method of controlling noxious insects which lay their eggs on standing crops by providing in the area of the crops a light flow the light intensity of which is varied, with cyclic repetition, gradually between a minimum and a maximum, the light intensity returning momentarily between two succeeding cycles.

6 Claims, 1 Drawing Figure

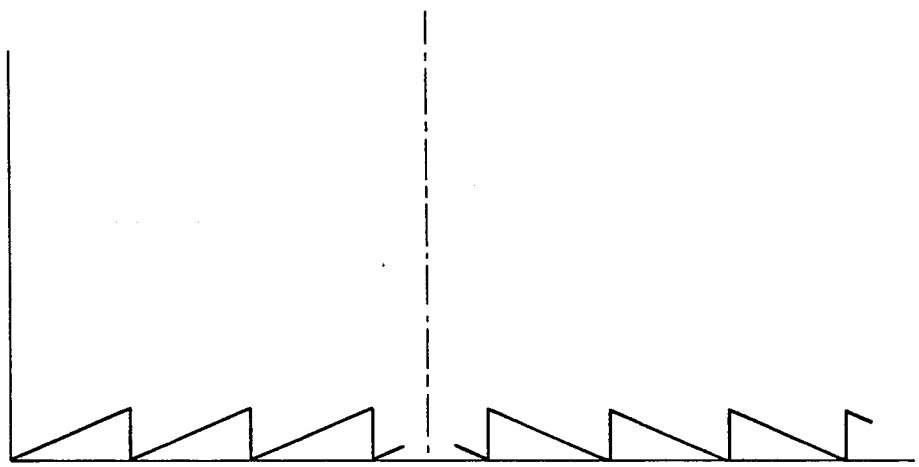

METHOD OF CONTROLLING NOXIOUS INSECTS

The invention relates to a method of controlling noxious insects which lay their eggs on standing crops.

By studying the behaviour of insects it has been found that the inclination to oviposition of the females of night-active insects, said ovipositon with few exceptions taking place in the night, is influenced i.a. by the moonlight which has an inhibiting effect on the oviposition such that the oviposition activity is greater in dark nights than when the nights are bright due to moonlight. This phenomenon is explained in more detail in Ent. Scand. 5. 1974. 196–206 and in Bull. ent. Res. 66. 1976. 33–63.

BRIEF DESCRIPTION OF THE DRAWING

The sole FIGURE is a schematic diagram plotting light intensity (vertical axis) versus time of day (horizontal axis) with midnight indicated by the dash line.

Considering these facts, the method proposed according to the invention has obtained the characteristics according to claim 1.

When the method according to the invention is applied, the insects are controlled without being caught or killed by the cylically repeated light variations affecting the insects in the same manner as the moonlight: the females will be less inclined to lay their eggs on the crops located in the varying light flow and thus these crops will not in a greater or less degree be eaten by the insect larvae.

It is important that the light intensity varies slowly from a minimum, preferably zero, to a maximum, and it is important as well that the light momentarily returns from the maximum to the minimum, because the insects adapt themselves to a constant light or a uniform, e.g. sinusodial, light variation. The period between the minimum and the maximum may be e.g. 20 sec. It is not necessary, however, that the light flow as a whole is cyclically varied; only a component of the light flow may be cyclically varied.

The slowly varying light flow can be provided by means of an artificial light source which is controlled or supplied by a solid state sweep circuit which can be of an embodiment known in the field of electronics.

By the inclination to oviposition of the insects being reduced due to the cyclically varying light flow, the area which is illuminated by this light flow also will accommodate fewer insects flying around, because the insects will not go to the illuminated area in order to lay their eggs there.

However, it has been found as well that also the mating inclination of night-active insects can be reduced by a varying light flow, but a light flow having an opposite cyclic variation i.e. the light intensity decreases gradually from a maximum to a minimum (zero value) and is then momentarily returned to the maximum. Also this influence on the behaviour of the insects involves a control of the insects without these being caught or killed, because reduced mating causes a reduced oviposition, and also in this case it is achieved that fewer insects flying around are accommodated in the area illuminated by the cyclically varying light.

The inhibition of the inclination to oviposition and mating by utilizing the natural inherent reaction of the insects to the influence of light also in the long run provides a stress situation which affects the reproduction as well as the life. Lively insects leave said area while insects which are going to lay their eggs, avoid the area.

Furthermore, it has been found that day-active insects which cannot fly such as plant lice, which stay within the area illuminated by varying light, will have their daily rhythm disturbed, which reduces the reproduction ability and shortens the life. The result thereof is that the number of these insects decreases.

The two control measures mentioned above can be combined with each other in an advantageous manner in such a way that before midnight when the major number of eggs are laid, there is provided a light flow in the area wherein the control of insects shall take place, the light intensity of said light flow being varied cyclically from a minimum to a maximum, while the light intensity after midnight when mating takes place, is varied cyclically from a maximum to a minimum. This is illustrated in the accompanying drawing which shows the light intensity (the vertical axis) over the time (the horizontal axis). To the left of the vertical dot and dash line indicating midnight, i.e. before midnight, the light pulses increase slowly from minimum to maximum in order then to return abruptly to minimum according to a saw-tooth characteristic, and under the influence of this light variation the inclination to oviposition of the insects will be affected. After midnight to the right of the vertical line, the light variation follows a reversed saw-tooth characteristic and then the mating inclination will be affected.

We claim:

1. A method of controlling noxious insects by repressing the insect's oviposition and mating comprising providing illumination of variable intensity onto the infested area, gradually varying the intensity between a first value and a second value, one of said values being higher than the other one, and abruptly changing the intensity from said second value to said first value and periodically repeating the cycle as with a linear electronic saw tooth sweep circuit generator.

2. A method according to claim 1 wherein one of said values is zero.

3. A method according to claim 1 wherein said first value is higher said second value.

4. A method according to claim 1 wherein said first value is lower than said second value.

5. A method according to claim 1 wherein said gradual varying of intensity includes periodic repetition of a first cycle of varying intensity by gradually increasing intensity from a minimum to a maximum and then abruptly reducing to a minimum, and thereafter a periodic repetition of a second cycle of varying intensity by gradually decreasing intensity from a maximum value to a minimum value and then abruptly increasing to a maximum value.

6. A method ccording to claim 1 or 5 wherein the cycle is generally 20 seconds.

* * * * *